(12) United States Patent
Robinson et al.

(10) Patent No.: US 11,364,152 B2
(45) Date of Patent: Jun. 21, 2022

(54) REDUCED-PRESSURE DRESSINGS EMPLOYING TISSUE-FIXATION ELEMENTS

(71) Applicant: KCI Licensing, Inc., San Antonio, TX (US)

(72) Inventors: Timothy Mark Robinson, Basingstoke (GB); Tyler H. Simmons, San Antonio, TX (US); Colin John Hall, Poole (GB); Jeanette Losole, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 689 days.

(21) Appl. No.: 15/682,812

(22) Filed: Aug. 22, 2017

(65) Prior Publication Data

US 2017/0348154 A1 Dec. 7, 2017

Related U.S. Application Data

(60) Continuation of application No. 14/853,407, filed on Sep. 14, 2015, now Pat. No. 10,973,696, which is a
(Continued)

(51) Int. Cl.
*A61F 13/02* (2006.01)
*A61M 1/00* (2006.01)
*A61F 13/00* (2006.01)

(52) U.S. Cl.
CPC .... *A61F 13/0253* (2013.01); *A61F 13/00068* (2013.01); *A61F 13/025* (2013.01);
(Continued)

(58) Field of Classification Search
CPC combination set(s) only.
See application file for complete search history.

(56) References Cited

U.S. PATENT DOCUMENTS

| 1,355,846 A | 10/1920 | Rannells |
| 2,547,758 A | 4/1951 | Kelling |

(Continued)

FOREIGN PATENT DOCUMENTS

| AU | 550575 B2 | 3/1986 |
| AU | 745271 B2 | 3/2002 |

(Continued)

OTHER PUBLICATIONS

U.S. Non-Final Rejection for Corresponding U.S. Appl. No. 14/853,407, dated Jan. 23, 2019.
(Continued)

*Primary Examiner* — Guy K Townsend

(57) ABSTRACT

A reduced-pressure system for treating a tissue site on a patient includes a distribution manifold that adheres to a tissue site to allow retention without external support. The distribution manifold includes a porous member and a tissue-fixation element. The tissue-fixation element maintains the porous member substantially adjacent to the tissue site while a sealing member is applied. In one instance, the tissue-fixation element is a soluble adhesive that partially covers either the tissue-facing side of the porous member or a tissue-facing side of a fluid-permeable substrate layer that is on the tissue-facing side of the porous member. Other systems, distributions manifolds, and methods are presented.

46 Claims, 6 Drawing Sheets

Related U.S. Application Data division of application No. 13/532,074, filed on Jun. 25, 2012, now Pat. No. 9,168,179.

(60) Provisional application No. 61/500,915, filed on Jun. 24, 2011.

(52) U.S. Cl.
CPC ........... *A61F 13/0216* (2013.01); *A61M 1/90* (2021.05); *A61F 2013/00174* (2013.01); *A61F 2013/00412* (2013.01); *A61F 2013/00536* (2013.01); *Y10T 29/49826* (2015.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| D614,284 S * | 4/2010 | Mormino | D24/107 |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,377,015 B2 * | 2/2013 | Ueda | A61F 13/0203 156/60 |
| 8,377,016 B2 * | 2/2013 | Argenta | A61H 7/001 424/447 |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,591,486 B2 * | 11/2013 | Locke | A61M 1/0023 604/319 |
| 8,679,081 B2 | 3/2014 | Heagle et al. | |
| 8,758,328 B2 * | 6/2014 | Locke | A61F 13/00068 604/543 |
| 8,764,732 B2 * | 7/2014 | Hartwell | A61F 13/00063 604/319 |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,168,179 B2 * | 10/2015 | Robinson | A61F 13/0216 |
| 9,198,801 B2 | 12/2015 | Weston | |
| 9,211,365 B2 | 12/2015 | Weston | |
| 9,289,542 B2 | 3/2016 | Blott et al. | |
| 9,427,506 B2 * | 8/2016 | Robinson | G01M 3/20 |
| 9,561,135 B2 * | 2/2017 | Robinson | A61F 13/00068 |
| 9,956,121 B2 * | 5/2018 | Hartwell | A61F 13/00063 |
| 10,231,875 B2 * | 3/2019 | Hartwell | A61M 1/90 |
| 10,278,870 B2 * | 5/2019 | Robinson | A61F 13/00068 |
| 10,293,088 B2 * | 5/2019 | Locke | A61M 1/0023 |
| 10,383,986 B2 * | 8/2019 | Robinson | A61F 13/00068 |
| 10,406,062 B2 * | 9/2019 | Hardman | A61B 5/447 |
| 10,406,266 B2 * | 9/2019 | Locke | A61F 13/00068 |
| 10,406,337 B2 * | 9/2019 | Locke | A61M 1/90 |
| 10,973,696 B2 * | 4/2021 | Robinson | A61F 13/00068 |

(56) References Cited

U.S. PATENT DOCUMENTS

| | | | |
|---|---|---|---|
| 2002/0022422 A1* | 2/2002 | Waldrop | B29C 70/443 |
| | | | 264/510 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0120241 A1* | 8/2002 | Tyrrell | A61L 15/42 |
| | | | 424/443 |
| 2002/0143286 A1 | 10/2002 | Tumey | |
| 2004/0054338 A1 | 3/2004 | Bybordi et al. | |
| 2004/0073151 A1* | 4/2004 | Weston | A61M 1/90 |
| | | | 602/41 |
| 2004/0158221 A1* | 8/2004 | Mizutani | A61F 13/55165 |
| | | | 604/385.17 |
| 2005/0251082 A1* | 11/2005 | Del Bono | A61F 15/001 |
| | | | 602/41 |
| 2007/0098953 A1* | 5/2007 | Stabelfeldt | A61F 13/62 |
| | | | 428/100 |
| 2007/0219497 A1* | 9/2007 | Johnson | A61M 37/00 |
| | | | 604/131 |
| 2007/0219512 A1* | 9/2007 | Heaton | A61M 1/90 |
| | | | 604/304 |
| 2008/0011368 A1* | 1/2008 | Singh | A61M 39/1055 |
| | | | 137/565.01 |
| 2008/0071214 A1* | 3/2008 | Locke | A61N 1/0468 |
| | | | 604/111 |
| 2008/0071216 A1* | 3/2008 | Locke | A61M 1/90 |
| | | | 604/119 |
| 2008/0071235 A1* | 3/2008 | Locke | A61N 5/0616 |
| | | | 604/318 |
| 2008/0195017 A1* | 8/2008 | Robinson | A61F 13/0203 |
| | | | 602/44 |
| 2008/0200906 A1* | 8/2008 | Sanders | A61M 1/73 |
| | | | 604/543 |
| 2009/0216170 A1* | 8/2009 | Robinson | A61F 13/0246 |
| | | | 602/60 |
| 2009/0221990 A1* | 9/2009 | Jaeb | A61M 1/784 |
| | | | 604/540 |
| 2009/0227969 A1* | 9/2009 | Jaeb | A61M 1/962 |
| | | | 604/313 |
| 2009/0234259 A1* | 9/2009 | Hardman | A61H 9/0057 |
| | | | 601/134 |
| 2009/0254053 A1* | 10/2009 | Svensby | A61F 13/0203 |
| | | | 604/290 |
| 2009/0254066 A1* | 10/2009 | Heaton | A61M 1/80 |
| | | | 604/543 |
| 2009/0275922 A1* | 11/2009 | Coulthard | A61M 1/74 |
| | | | 604/543 |
| 2009/0299303 A1* | 12/2009 | Seegert | A61M 27/00 |
| | | | 602/53 |
| 2010/0030166 A1* | 2/2010 | Tout | A61M 27/00 |
| | | | 604/316 |
| 2010/0042033 A1 | 2/2010 | Praetzel | |
| 2010/0069850 A1* | 3/2010 | Fabo | A61L 15/42 |
| | | | 604/180 |
| 2010/0069863 A1* | 3/2010 | Olson | A61M 1/90 |
| | | | 604/385.01 |
| 2010/0106106 A1* | 4/2010 | Heaton | A61F 13/00068 |
| | | | 604/290 |
| 2010/0106116 A1* | 4/2010 | Simmons | A61M 1/90 |
| | | | 604/319 |
| 2010/0121286 A1* | 5/2010 | Locke | A61F 13/00987 |
| | | | 604/319 |
| 2010/0125258 A1* | 5/2010 | Coulthard | A61M 1/88 |
| | | | 604/319 |
| 2010/0160874 A1* | 6/2010 | Robinson | A61M 1/90 |
| | | | 604/313 |
| 2010/0160876 A1* | 6/2010 | Robinson | A61M 1/0023 |
| | | | 604/319 |
| 2010/0168746 A1* | 7/2010 | Griffey | A61B 17/56 |
| | | | 606/60 |
| 2010/0174250 A1* | 7/2010 | Hu | A61M 1/90 |
| | | | 602/54 |
| 2010/0298791 A1* | 11/2010 | Jones | A61F 13/00063 |
| | | | 604/319 |
| 2010/0305490 A1* | 12/2010 | Coulthard | A61F 13/022 |
| | | | 602/43 |
| 2010/0305526 A1* | 12/2010 | Robinson | A61M 1/0001 |
| | | | 604/319 |
| 2011/0004172 A1* | 1/2011 | Eckstein | A61M 1/0023 |
| | | | 604/313 |
| 2011/0015595 A1* | 1/2011 | Robinson | A61M 1/90 |
| | | | 604/319 |
| 2011/0028918 A1* | 2/2011 | Hartwell | A61M 27/00 |
| | | | 604/319 |
| 2011/0054420 A1* | 3/2011 | Locke | A61M 1/90 |
| | | | 604/311 |
| 2011/0054421 A1* | 3/2011 | Hartwell | A61F 13/0216 |
| | | | 604/319 |
| 2011/0054422 A1* | 3/2011 | Locke | A61F 13/022 |
| | | | 604/319 |
| 2011/0066123 A1* | 3/2011 | Tout | A61M 1/90 |
| | | | 604/319 |
| 2011/0118683 A1* | 5/2011 | Weston | A61M 1/732 |
| | | | 604/319 |
| 2011/0160686 A1* | 6/2011 | Ueda | A61F 13/0203 |
| | | | 156/60 |
| 2011/0178451 A1* | 7/2011 | Robinson | B29C 44/5636 |
| | | | 602/46 |
| 2011/0178481 A1* | 7/2011 | Locke | B32B 38/0008 |
| | | | 604/319 |
| 2011/0184357 A1* | 7/2011 | Robinson | A61F 13/00068 |
| | | | 604/290 |
| 2011/0196278 A1* | 8/2011 | Svedman | A61F 13/0216 |
| | | | 602/43 |
| 2011/0224630 A1* | 9/2011 | Simmons | A61M 1/90 |
| | | | 604/317 |
| 2011/0224631 A1* | 9/2011 | Simmons | A61F 13/00021 |
| | | | 604/319 |
| 2011/0224633 A1* | 9/2011 | Robinson | A61M 1/90 |
| | | | 604/319 |
| 2011/0224634 A1* | 9/2011 | Locke | A61F 13/00029 |
| | | | 604/319 |
| 2011/0230849 A1* | 9/2011 | Coulthard | A61M 1/962 |
| | | | 604/319 |
| 2011/0245682 A1* | 10/2011 | Robinson | G01M 3/002 |
| | | | 600/473 |
| 2011/0257572 A1* | 10/2011 | Locke | A61F 13/0226 |
| | | | 602/46 |
| 2011/0257611 A1* | 10/2011 | Locke | A61M 1/90 |
| | | | 604/319 |
| 2011/0282309 A1* | 11/2011 | Adie | A61M 1/90 |
| | | | 604/319 |
| 2011/0288510 A1* | 11/2011 | Locke | A61M 1/74 |
| | | | 604/319 |
| 2011/0288512 A1* | 11/2011 | Locke | B01D 53/268 |
| | | | 604/319 |
| 2011/0319753 A1* | 12/2011 | Tout | A61K 49/04 |
| | | | 600/431 |
| 2012/0016323 A1* | 1/2012 | Robinson | A61F 13/0216 |
| | | | 604/319 |
| 2012/0101458 A1* | 4/2012 | Hall | A61M 1/90 |
| | | | 604/319 |
| 2012/0101512 A1* | 4/2012 | Locke | B26B 11/008 |
| | | | 606/169 |
| 2012/0123358 A1* | 5/2012 | Hall | A61M 1/90 |
| | | | 604/318 |
| 2012/0123360 A1* | 5/2012 | Locke | A61M 1/0023 |
| | | | 604/319 |
| 2012/0143113 A1* | 6/2012 | Robinson | A61M 1/85 |
| | | | 602/43 |
| 2012/0157750 A1* | 6/2012 | Robinson | A61N 1/40 |
| | | | 600/12 |
| 2012/0157826 A1* | 6/2012 | Locke | A61F 13/00068 |
| | | | 600/424 |
| 2012/0157945 A1* | 6/2012 | Robinson | A61F 13/02 |
| | | | 604/319 |
| 2012/0209226 A1* | 8/2012 | Simmons | A61M 1/90 |
| | | | 604/319 |

(56) References Cited

U.S. PATENT DOCUMENTS

| | | | |
|---|---|---|---|
| 2012/0271320 A1* | 10/2012 | Hall | A61B 17/32053 606/132 |
| 2012/0302979 A1* | 11/2012 | Locke | A61M 1/85 604/319 |
| 2012/0330252 A1* | 12/2012 | Stokes | A61F 13/00068 604/318 |
| 2012/0330253 A1* | 12/2012 | Robinson | A61F 13/0216 604/319 |
| 2013/0028953 A1* | 1/2013 | Yum | A61K 31/4535 424/443 |
| 2013/0035649 A1* | 2/2013 | Locke | A61F 13/00068 604/290 |
| 2013/0053793 A1* | 2/2013 | Locke | A61M 1/90 604/290 |
| 2013/0053799 A1* | 2/2013 | Locke | A61M 1/0058 604/319 |
| 2013/0066285 A1* | 3/2013 | Locke | A61F 13/00068 604/318 |
| 2013/0066301 A1* | 3/2013 | Locke | A61M 1/78 604/543 |
| 2013/0072850 A1* | 3/2013 | Locke | A61L 15/42 604/20 |
| 2013/0123723 A1* | 5/2013 | Tout | A61M 1/90 604/319 |
| 2013/0123728 A1* | 5/2013 | Pratt | A61F 13/0216 604/369 |
| 2013/0131471 A1* | 5/2013 | Locke | A61B 5/742 600/317 |
| 2013/0131564 A1* | 5/2013 | Locke | A61L 15/28 601/149 |
| 2013/0144227 A1* | 6/2013 | Locke | A61M 1/74 604/318 |
| 2013/0150815 A1* | 6/2013 | Luckemeyer | A61F 13/00991 604/319 |
| 2013/0152945 A1* | 6/2013 | Locke | A61M 1/90 128/849 |
| 2013/0165836 A1* | 6/2013 | Locke | A61L 15/42 602/44 |
| 2013/0211349 A1* | 8/2013 | Stokes | B29C 44/5636 604/290 |
| 2013/0317406 A1* | 11/2013 | Locke | A61M 1/90 602/46 |
| 2014/0012213 A1* | 1/2014 | Locke | A61F 13/025 604/319 |
| 2014/0012215 A1* | 1/2014 | Kendrick | A61F 13/0209 604/319 |
| 2014/0031771 A1* | 1/2014 | Locke | A61F 13/0209 604/318 |
| 2014/0046282 A1* | 2/2014 | Locke | A61M 1/0023 604/319 |
| 2014/0155791 A1* | 6/2014 | Robinson | A61F 13/0269 601/7 |
| 2014/0163490 A1* | 6/2014 | Locke | A61F 13/0206 604/319 |
| 2014/0163491 A1 | 6/2014 | Schuessler et al. | |
| 2014/0163532 A1* | 6/2014 | Cornet | A61M 25/0071 604/543 |
| 2014/0188057 A1* | 7/2014 | Sivaraman | A61K 9/7023 604/307 |
| 2014/0188058 A1* | 7/2014 | Robinson | A61F 13/0203 604/319 |
| 2014/0188059 A1* | 7/2014 | Robinson | A61F 13/0233 604/319 |
| 2014/0188060 A1* | 7/2014 | Robinson | A61F 13/0216 604/319 |
| 2014/0188061 A1* | 7/2014 | Locke | A61M 1/815 604/321 |
| 2014/0200526 A1* | 7/2014 | Locke | A61N 5/062 604/290 |
| 2014/0200532 A1* | 7/2014 | Robinson | A61M 1/0023 604/319 |
| 2014/0276275 A1* | 9/2014 | Stokes | A61F 13/00038 601/84 |
| 2014/0276489 A1* | 9/2014 | Robinson | A61M 1/73 604/319 |
| 2014/0276490 A1* | 9/2014 | Locke | A61L 15/58 604/319 |
| 2014/0276491 A1* | 9/2014 | Luckemeyer | A61M 1/90 604/319 |
| 2014/0276492 A1* | 9/2014 | Pratt | A61M 1/88 604/319 |
| 2014/0276497 A1* | 9/2014 | Robinson | A61M 1/882 604/321 |
| 2014/0277454 A1* | 9/2014 | Locke | A61B 17/322 623/15.12 |
| 2015/0057624 A1* | 2/2015 | Simmons | A61F 13/0206 604/319 |
| 2015/0080788 A1 | 3/2015 | Blott et al. | |
| 2015/0119830 A1* | 4/2015 | Luckemeyer | A61M 1/90 604/319 |
| 2015/0119831 A1* | 4/2015 | Robinson | A61F 13/0216 604/319 |
| 2015/0119834 A1* | 4/2015 | Locke | A61L 15/58 604/319 |
| 2015/0182241 A1* | 7/2015 | Pratt | A61B 17/322 606/132 |
| 2015/0182242 A1* | 7/2015 | Pratt | A61B 17/322 606/132 |
| 2015/0201954 A1* | 7/2015 | Pratt | A61B 17/322 606/131 |
| 2015/0231314 A1* | 8/2015 | Robinson | A61F 13/00017 604/319 |
| 2015/0245949 A1* | 9/2015 | Locke | A61F 13/0216 604/319 |
| 2015/0245950 A1* | 9/2015 | Locke | A61M 1/90 604/319 |
| 2015/0320434 A1* | 11/2015 | Ingram | A61B 17/22004 606/131 |
| 2015/0320602 A1* | 11/2015 | Locke | A61M 1/90 606/213 |
| 2015/0320603 A1* | 11/2015 | Locke | A61B 17/32 604/543 |
| 2016/0015871 A1* | 1/2016 | Locke | A61M 1/85 604/290 |
| 2016/0015873 A1* | 1/2016 | Robinson | A61M 1/743 604/290 |
| 2016/0038626 A1* | 2/2016 | Locke | A61H 9/0057 601/6 |
| 2016/0095754 A1* | 4/2016 | Andrews | A61L 15/44 604/319 |
| 2016/0175156 A1* | 6/2016 | Locke | A61F 13/0223 604/318 |
| 2016/0199550 A1* | 7/2016 | Seddon | A61F 13/00068 604/319 |
| 2016/0287763 A1* | 10/2016 | Simmons | A61M 1/73 |
| 2016/0325028 A1* | 11/2016 | Locke | A61M 1/90 |
| 2017/0014606 A1* | 1/2017 | Locke | A61F 13/00063 |
| 2017/0043070 A1* | 2/2017 | Locke | A61F 13/0216 |
| 2017/0079846 A1* | 3/2017 | Locke | A61L 15/58 |
| 2017/0128269 A1* | 5/2017 | Coulthard | A61F 13/00029 |
| 2017/0151095 A1* | 6/2017 | Robinson | A61F 13/00068 |
| 2017/0189236 A1* | 7/2017 | Locke | A61F 13/0253 |
| 2017/0189237 A1* | 7/2017 | Locke | B32B 3/266 |
| 2017/0296714 A1* | 10/2017 | Locke | A61F 13/0216 |
| 2017/0326004 A1* | 11/2017 | Long | A61F 13/0273 |
| 2018/0110657 A1* | 4/2018 | Locke | A61B 46/40 |
| 2018/0140822 A1* | 5/2018 | Robinson | F16K 31/1221 |
| 2018/0185629 A1* | 7/2018 | Luckemeyer | A61M 1/743 |
| 2018/0200419 A1* | 7/2018 | Locke | A61F 13/00068 |
| 2018/0214313 A1* | 8/2018 | Pratt | A61F 13/0216 |
| 2018/0214315 A1* | 8/2018 | Mercer | A61F 13/00029 |
| 2018/0235646 A1* | 8/2018 | Locke | A61M 1/85 |
| 2018/0272052 A1* | 9/2018 | Locke | A61F 13/0216 |
| 2018/0280200 A1* | 10/2018 | Robinson | A61M 1/882 |
| 2018/0318475 A1* | 11/2018 | Thomson | A61M 1/73 |
| 2018/0333522 A1* | 11/2018 | Pratt | A61M 1/74 |
| 2018/0353338 A1* | 12/2018 | Locke | A61M 1/90 |
| 2018/0353339 A1* | 12/2018 | Locke | A61F 13/00068 |

(56) References Cited

U.S. PATENT DOCUMENTS

| | | | | |
|---|---|---|---|---|
| 2018/0353340 | A1* | 12/2018 | Robinson | A61F 13/00068 |
| 2018/0353341 | A1* | 12/2018 | Locke | A61F 13/00068 |
| 2018/0353342 | A1* | 12/2018 | Locke | A61L 15/24 |
| 2018/0353344 | A1* | 12/2018 | Locke | A61F 13/00987 |
| 2018/0353662 | A1* | 12/2018 | Locke | A61M 1/90 |
| 2018/0353663 | A1* | 12/2018 | Locke | A61F 13/0216 |
| 2019/0038473 | A1* | 2/2019 | Luckemeyer | A61F 13/00068 |
| 2019/0046699 | A1* | 2/2019 | Robinson | A61M 1/0058 |
| 2019/0060127 | A1* | 2/2019 | Locke | A61F 13/0216 |
| 2019/0125945 | A1* | 5/2019 | Long | A61M 1/784 |
| 2019/0167483 | A1* | 6/2019 | Simmons | A61F 13/0216 |
| 2019/0216652 | A1* | 7/2019 | Robinson | A61F 13/00068 |
| 2019/0216991 | A1* | 7/2019 | Locke | G01L 21/00 |
| 2019/0224388 | A1* | 7/2019 | Locke | A61M 1/0023 |
| 2019/0231600 | A1* | 8/2019 | Locke | A61F 13/0216 |
| 2019/0231943 | A1* | 8/2019 | Robinson | A61L 15/26 |
| 2019/0255230 | A1* | 8/2019 | Simmons | A61F 13/00068 |
| 2019/0262181 | A1* | 8/2019 | Long | A61M 1/90 |
| 2019/0262183 | A1* | 8/2019 | Robinson | A61F 13/00017 |
| 2019/0274891 | A1* | 9/2019 | Simmons | A61F 13/00068 |

FOREIGN PATENT DOCUMENTS

| | | | | |
|---|---|---|---|---|
| AU | 755496 | B2 | 12/2002 | |
| CA | 2005436 | A1 | 6/1990 | |
| DE | 26 40 413 | A1 | 3/1978 | |
| DE | 43 06 478 | A1 | 9/1994 | |
| DE | 29 504 378 | U1 | 9/1995 | |
| EP | 0100148 | A1 | 2/1984 | |
| EP | 0117632 | A2 | 9/1984 | |
| EP | 0161865 | A2 | 11/1985 | |
| EP | 0358302 | A2 | 3/1990 | |
| EP | 1018967 | A1 | 7/2000 | |
| GB | 692578 | A | 6/1953 | |
| GB | 2 195 255 | A | 4/1988 | |
| GB | 2 197 789 | A | 6/1988 | |
| GB | 2 220 357 | A | 1/1990 | |
| GB | 2 235 877 | A | 3/1991 | |
| GB | 2 329 127 | A | 3/1999 | |
| GB | 2 333 965 | A | 8/1999 | |
| JP | 4129536 | B2 | 8/2008 | |
| SG | 71559 | | 4/2002 | |
| WO | 80/02182 | A1 | 10/1980 | |
| WO | 87/04626 | A1 | 8/1987 | |
| WO | 90/010424 | A1 | 9/1990 | |
| WO | 93/009727 | A1 | 5/1993 | |
| WO | 94/020041 | A1 | 9/1994 | |
| WO | 96/05873 | A1 | 2/1996 | |
| WO | 97/18007 | A1 | 5/1997 | |
| WO | 99/13793 | A1 | 3/1999 | |
| WO | 2008008032 | A1 | 1/2008 | |
| WO | 2008/041926 | A1 | 4/2008 | |
| WO | WO-2009066106 | A1 * | 5/2009 | A61F 13/00063 |
| WO | 2009111655 | A2 | 9/2009 | |
| WO | 2011/028407 | A1 | 3/2011 | |
| WO | 2011/049562 | A1 | 4/2011 | |
| WO | 2013066426 | A2 | 5/2013 | |

OTHER PUBLICATIONS

Canadian Examiner's Report for Corresponding Application No. 2840187, dated Feb. 4, 2019.
U.S. Non-Final Rejection for corresponding U.S. Appl. No. 14/853,407, dated Dec. 18, 2017.
U.S. Final Rejection for Corresponding U.S. Appl. No. 14/853,407, dated Jul. 29, 2019.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al: Negative-Pressure Dressings as a Bolster for Skin Grafts; Annals of Plastic Surgery, vol. 40, No. 5, May 1998, pp. 453-457; Lippincott Williams & Wilkins, Inc., Philadelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 pages English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 pages English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 pages English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

(56) References Cited

OTHER PUBLICATIONS

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, " Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96,167-170, and 210-211.
V.A. Solovev et al., Guidelines, The Method of Treatment of Immature External Fistulas In the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Japanese First Office Action/Notice of Rejection, dated Jul. 5, 2016, corresponding to JP2014-517248. (Some English).
Japanese Notice of Rejection for corresponding Application No. 2017194765, dated Jul. 10, 2018.
Japanese Notice of Rejection for Corresponding Application No. 2019-105044, dated Jul. 21, 2020.
Japanese Notice of Rejection for Corresponding Application No. 2017-194765, dated Apr. 28, 2020.
Non-Final Office Action for Corresponding U.S. Appl. No. 14/853,407, dated Aug. 5, 2020.

\* cited by examiner

REDUCED-PRESSURE DRESSINGS EMPLOYING TISSUE-FIXATION ELEMENTS

RELATED APPLICATIONS

This application is a continuation of U.S. patent application Ser. No. 14/853,407, filed Sep. 14, 2015, which is a divisional of U.S. patent application Ser. No. 13/532,074, filed Jun. 25, 2012, now U.S. Pat. No. 9,168,179, which claims the benefit, under 35 USC § 119(e), of the filing of U.S. Provisional Patent Application No. 61/500,915, entitled "Reduced-Pressure Dressings Employing Tissue-Fixation Elements," filed Jun. 24, 2011. Each of the applications above are incorporated herein by reference for all purposes.

BACKGROUND

The present disclosure relates generally to medical treatment systems and, more particularly, but not by way of limitation, to reduced-pressure dressings employing a tissue-fixation element.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad distributes reduced pressure to the tissue and channels fluids that are drawn from the tissue. Reduced pressure may also be applied for other treatments, such as removing fluids.

SUMMARY

According to an illustrative embodiment, a reduced-pressure system for treating a tissue site includes a distribution manifold, a sealing member for disposing over the distribution manifold to create a sealed space containing the distribution manifold, a reduced-pressure source fluidly coupled to the sealed space for providing reduced pressure to the sealed space, and a liquid receptor fluidly coupled to distribution manifold for receiving fluids from the patient under the influence of reduced pressure. The distribution manifold includes a porous member having a plurality of flow channels for distributing reduced pressure and receiving fluids. The porous member has a first side and a second, tissue-facing side. The distribution manifold further includes a fluid-permeable substrate member having a first side and a second, tissue-facing side. The second, tissue-facing side of the porous member is disposed proximate to the first side of the fluid-permeable substrate member. The second, tissue-facing side of the fluid-permeable substrate member has a surface area A. The distribution manifold also includes a tissue-fixation element having a first side and a second, tissue-facing side, and wherein the first side of the tissue-fixation element is coupled to the second, tissue-facing side of the fluid-permeable substrate member. The second, tissue-facing side of the tissue-fixation element has a surface area $A_t$. The surface areas, $A_t$ and $A_s$, are related according to the following expression: $0.05\ A_s < A_t < 0.6\ A_s$.

According to another illustrative embodiment, a method for treating a tissue site on a patient with reduced pressure includes the steps of tacking a distribution manifold to the tissue site using a tissue-fixation element on the distribution manifold so that the distribution manifold remains substantially adjacent to the tissue site, covering the distribution manifold with a sealing member to form a sealed space containing the distribution manifold, and providing reduced pressure to the sealed space. The distribution manifold includes a porous member for distributing reduced pressure and receiving fluid. The porous member has a surface area $A_p$ facing the tissue site. The distribution manifold also includes a tissue-fixation element coupled to the porous member. The tissue-fixation element has a surface area $A_t$ facing the tissue site, and wherein $0.05\ A_p < A_t < 0.6\ A_p$.

According to another illustrative embodiment, a method of treating a tissue site on a patient with reduced pressure includes the steps of providing a tack unit, providing a distribution manifold comprising a porous member, disposing the tack unit against the tissue site, and disposing the distribution manifold against the tack unit such that the distribution manifold remains adjacent to the tissue site without exterior support other than the tack unit and the tissue site. The method further includes covering the distribution manifold with a sealing member to create a sealed space containing the distribution manifold, and providing reduced pressure to the sealed space.

According to another illustrative embodiment, a distribution manifold for use in a reduced pressure system for providing reduced pressure to a tissue site on a patient includes a porous member having a plurality of flow channels for distributing reduced pressure and receiving fluids. The porous member has a first side and a second, tissue-facing side. The distribution manifold further includes a fluid-permeable substrate member having a first side and a second, tissue-facing side. The second, tissue-facing side of the porous member is proximate to the first side of the fluid-permeable substrate member. The second, tissue-facing side of the fluid-permeable substrate member has a surface area $A_s$. The distribution manifold also includes a tissue-fixation element having a first side and a second, tissue-facing side. The first side of the tissue-fixation element is coupled to the second, tissue-facing side of the fluid-permeable substrate member. The second, tissue-facing side of the tissue-fixation element has a surface area $A_t$, and wherein $0.05\ A_s < A_t < 0.6\ A_s$.

According to another illustrative embodiment, a method of manufacturing a distribution manifold for use in a reduced-pressure system for providing reduced pressure to a tissue site on a patient includes the steps of providing a porous member having a plurality of flow channels for distributing reduced pressure and receiving fluids. The porous member has a first side and a second, tissue-facing side. The method further includes providing a fluid-permeable substrate member having a first side and a second, tissue-facing side. The second, tissue-facing side of the fluid-permeable substrate member has a surface area $A_s$. The method further includes coupling the second, tissue-facing side of the porous member to the first side of the fluid-permeable substrate member and providing a tissue-fixation element having a first side and a second, tissue-facing side. The second, tissue-facing side of the tissue-fixation element has a surface area $A_t$. $A_s$ and $A_t$ have the following relationship: $0.05\ A_s < A_t < 0.6\ A_s$. The method further includes coupling the first side of the tissue-fixation element to the second, tissue-facing side of the fluid-permeable substrate member.

According to another illustrative embodiment, a method of treating a tissue site on a patient with reduced pressure includes the steps of positioning the patient in a prevailing position, which is a position that the patient will remain for a majority of time during treatment; and using a tissue-fixation element to tack a porous member to the tissue site while the patient remains in the prevailing position. In the prevailing position, the tissue site is substantially parallel to a gravitational field. The method further includes covering the porous member with a sealing member to form a sealed space and providing reduced pressure to the sealed space.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

Figure 1:
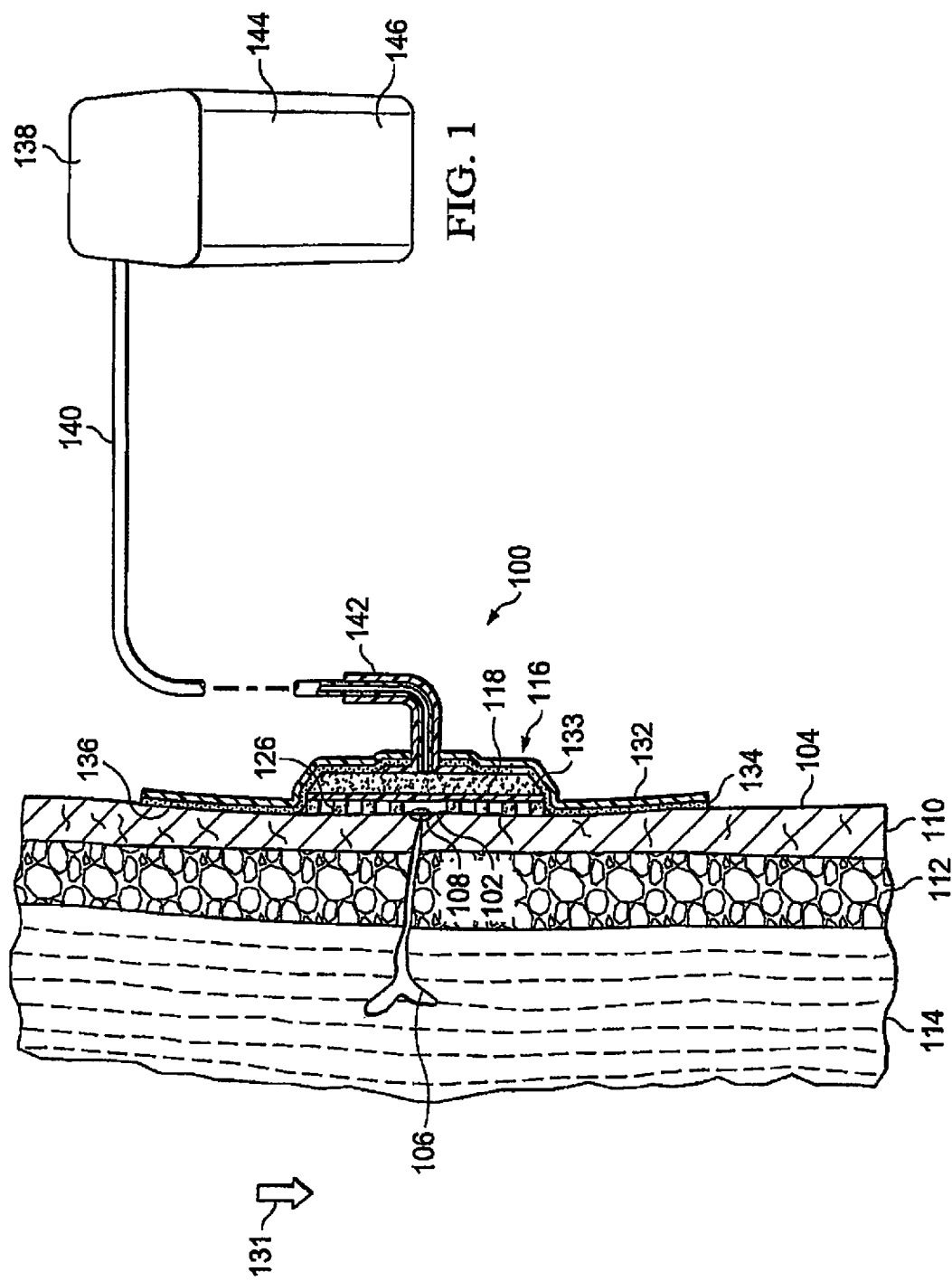
FIG. 1 is a schematic diagram with a portion shown in cross section of an illustrative embodiment of a reduced-pressure system for treating a tissue site.
Figure 2:
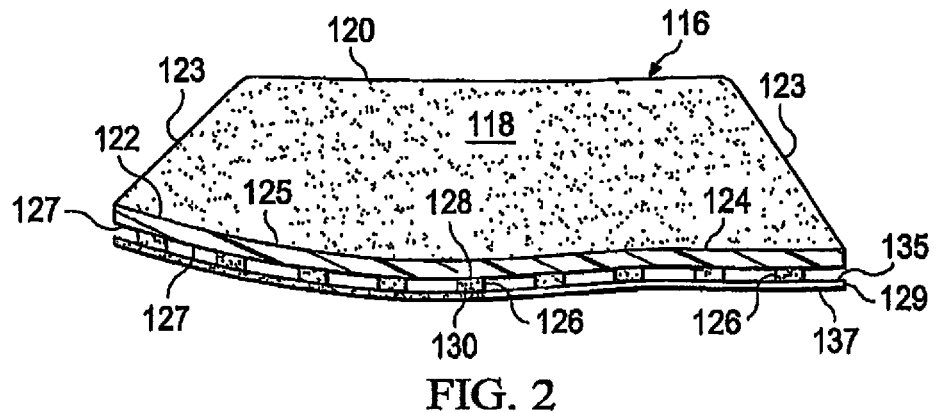
FIG. 2 is a schematic cross section of an illustrative embodiment of a distribution manifold.

Referring now primarily to FIGS. 1 and 2, a reduced-pressure system 100 for treating a tissue site 102 of a patient 104 with reduced pressure is presented. The reduced-pressure treatment may be used to promote tissue growth, help approximate a wound, remove fluids, or other purposes. Unless otherwise indicated, as used throughout this document, "or" does not require mutual exclusivity. The tissue site 102 may be, as a non-limiting example, an incision 106. The incision 106 is shown with a stitch 108 helping to hold the incision 106 in a closed position. The incision 106 may be through the patient's 104 epidermis 110, dermis 112, and into the subcutaneous tissue 114. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue.

The reduced-pressure system 100 includes a distribution manifold 116 that is disposed adjacent to the tissue site 102. The distribution manifold 116 includes a porous member 118 having a plurality of flow channels for distributing reduced pressure and receiving fluids. The porous member 118 has a first side 120 and a second, tissue-facing side 122. As shown best in FIG. 2, the distribution manifold 116 may also include a fluid-permeable substrate member 124 having a first side 125 and a second, tissue-facing side 127. The second, tissue-facing side 122 of the porous member 118 is proximate to the first side 125 of the fluid-permeable substrate member 124. The second, tissue-facing side 127 of the fluid-permeable substrate member 124 has a surface area $A_s$.

The porous member of the distribution manifold 116 refers to a substance or structure that is provided to assist in applying reduced pressure to, delivering fluids to, or removing fluids from a tissue site. The porous member 118 typically includes a plurality of flow channels or pathways that distribute fluids provided to and removed from the tissue site 102 around the distribution manifold 116. In one illustrative embodiment, the flow channels or pathways are interconnected to improve distribution of fluids provided or removed from the tissue site 102. The porous member 118 may be a biocompatible material that may be placed directly in contact with the tissue site 102 and distributes reduced pressure. Examples of porous members 118 may include, without limitation, devices that have structural elements arranged to form flow channels, such as, for example, cellular foam, open-cell foam, porous tissue collections, liquids, gels, and foams that include, or cure to include, flow channels. The porous member 118 may be made from foam, gauze, felted mat, or any other material suited to a particular biological application. In one embodiment, the porous member 118 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. In some situations, the porous member 118 may also be used to distribute fluids such as medications, antibacterials, growth factors, and various solutions to the tissue site 102. Other layers may be included in or on the porous member 118, such as absorptive materials, wicking materials, hydrophobic materials, and hydrophilic materials.

In one illustrative embodiment, the porous member 118 may be constructed from a bioresorbable material that if used with an open wound does not have to be removed from a patient's body following use. Suitable bioresorbable materials may include, without limitation, a polymeric blend of polylactic acid (PLA) and polyglycolic acid (PGA). The polymeric blend may also include without limitation poly-carbonates, polyfumarates, and capralactones. The porous member 118 may further serve as a scaffold for new cell-growth, or a scaffold material may be used in conjunction with the porous member 118 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. The porous member 118 may take any shape, e.g., a rectangle, a square, triangle, a circle, or any other shape.

As shown in FIG. 2, the lateral edges 123 of the porous member 118 may be shaped edges to offload smoothly forces on the porous member 118 to the tissue site 102 or areas near the tissue site 102. For example, the lateral edges 123 of the porous member 118 may be formed, as a non-limiting example, at a 45 degree angle as shown or a 30 degree angle or another angle that helps off load forces. As explained later in connection with FIGS. 10 and 11, the porous member 118 may have notches formed on the first side 120 to enhance flexibility of the porous member 118.

The distribution manifold 116 may include the fluid-permeable substrate member 124. The fluid-permeable substrate member 124 is operational to prevent or inhibit irritation of the tissue site 102 by the porous member 118. The fluid-permeable substrate member 124 may be a woven material, non-woven material (using such fiber forming polymers as polyvinyl alcohols, polyvinyl acetates, polyethylenes, polyesters, polyamides, polyacrylics and polyacrylates, cellulosics and their copolymers, and where non ionizing radiation methods of sterilization are used, polypropylene), fenestrated drape or film (using such fiber-forming polymers as just listed), a high density foam (higher density than the porous member 118) or any material that inhibits irritation of the tissue site 102 by the porous member 118 while allowing fluid transmission. The fluid-permeable substrate member 124 may make attachment of a tissue-fixation element 126 (described further below) easier. The fluid-permeable substrate member 124 may be coupled to the distribution manifold 116 using an adhesive bond, flame lamination or heat lamination, spray adhesive, hot melt, or any other device or technique. The fluid-permeable substrate member 124 may be coupled to the distribution manifold 116 by forming an integral foam or film such as by using compressed or felting foams and co-blown foam and film.

The fluid-permeable substrate member 124 may contain medicaments, e.g., antimicrobials, lidocaine, or other substances, to treat the tissue site 102. The fluid-permeable substrate member 124 may be a solid substrate or may only partially cover the porous member 118. Coupled includes coupling via a separate object and includes direct coupling. The term coupled also encompasses two or more components that are continuous with one another by virtue of each of the components being formed from the same piece of material. Coupling may also include chemical, such as via a chemical bond, mechanical, thermal, or electrical coupling. Fluid coupling means that fluid may be in communication between the designated parts or locations.

The distribution manifold 116 includes the tissue-fixation element 126. As will be explained more further below, the tissue-fixation element 126 is operational to tack or at least temporarily attach the distribution manifold 116 to the tissue site 102 while other aspects of the reduced-pressure system 100 are applied. The tissue-fixation element 126 has a first side 128 and a second, tissue-facing side 130. The first side 128 of the tissue-fixation element 126 may be coupled to the second, tissue-facing side 127 of the fluid-permeable substrate member 124 or in some embodiments directly to the second, tissue-facing side 122 of the porous member 118. The second, tissue-facing side 130 of the tissue-fixation element 126 has a surface area $A_t$. The tackiness of tissue-fixation element 126 may be such that the tissue-fixation element 126 will separate from the tissue site 102 before the fluid-permeable substrate member 124 separates from the porous member 118. In other words, the strength of tackiness of the tissue-fixation element 126 to the tissue site 102 is less than the strength of the bond between the tissue-fixation element 126 and the fluid-permeable substrate member 124.

The relationship of the surface area $A_t$ of the tissue-fixation element 126 to the surface area $A_s$ of the fluid-permeable substrate member 124 may be 0.05 $A_s < A_t < 0.6$ $A_s$. Other relationships between the surface areas $A_t$, $A_s$ are contemplated. As non-limiting, illustrative examples, the following relationships may be realized: 0.10 $A_s < A_t < 0.8$ $A_s$, 0.10 $A_s < A_t < 0.5$ $A_s$, 0.15 $A_s < A_t < 0.4$ $A_s$, 0.20 $A_s < A_t < 0.4$ $A_s$, or other relationships. The relationship of the surface areas is such that for a given tackiness of a tissue-fixation element 126, the surface area $A_t$ provides adequate force to hold the distribution manifold 116 adjacent to the tissue site 102 notwithstanding gravitational forces from the gravitational field 131. In the illustrative embodiments that do not utilize the fluid-permeable substrate member 124, the relationships are analogous as between the surface area $A_p$ of the second, tissue-facing side 122 of the porous member 118 and the area $A_t$ of the tissue-fixation element 126, e.g., 0.05 $A_p < A_t < 0.7$ $A_p$.

Figure 3:
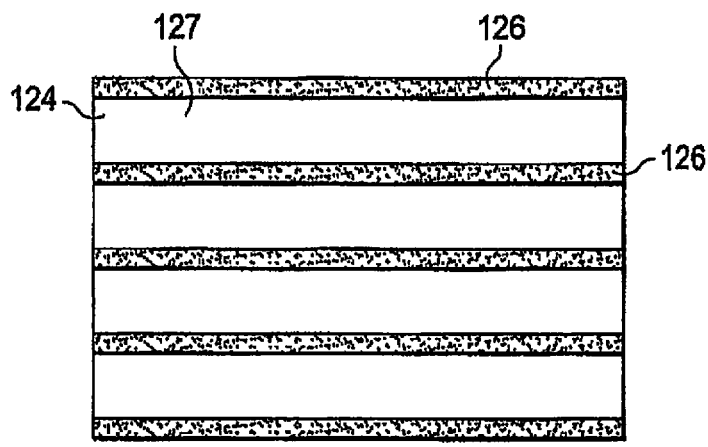
FIG. 3 is a schematic bottom (tissue-facing side) plan view of an illustrative embodiment of a porous member and a tissue-fixation element.
Figure 4:
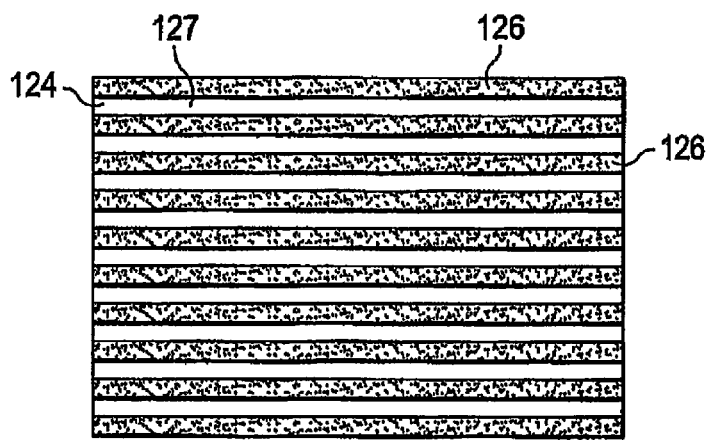
FIG. 4 is a schematic bottom plan view of an illustrative embodiment of a porous member and a tissue-fixation element.
Figure 5:
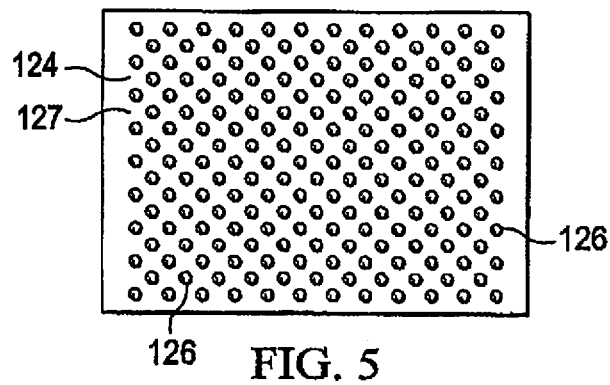
FIG. 5 is a schematic bottom plan view of an illustrative embodiment of a porous member and a tissue-fixation element.
Figure 6:
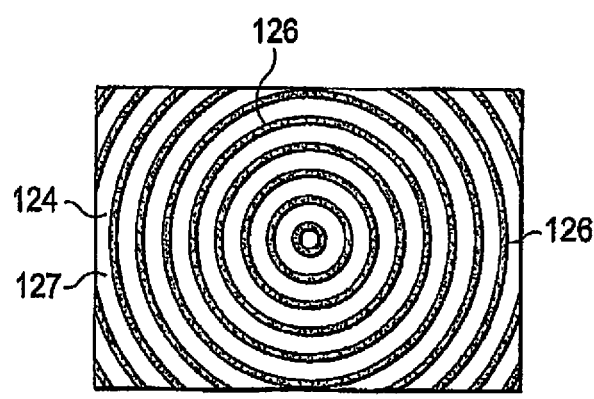
FIG. 6 is a schematic bottom plan view of an illustrative embodiment of a porous member and a tissue-fixation element.
Figure 7:
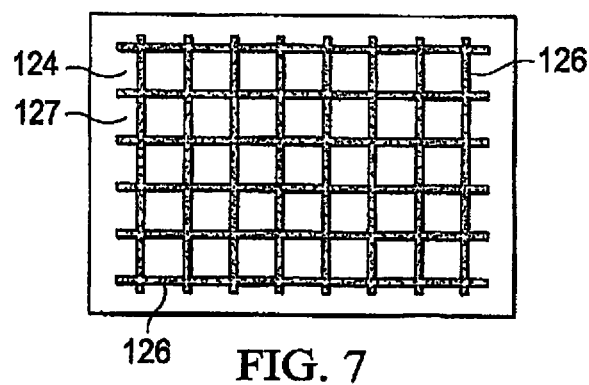
FIG. 7 is a schematic bottom plan view of an illustrative embodiment of a porous member and a tissue-fixation element.

The tissue-fixation element 126 may take numerous shapes or form numerous patterns. For example, the tissue-fixation element 126 may comprise spaced strips or lines coupled to the second, tissue-facing side 127 of the fluid-permeable substrate member 124 (or alternatively the second, tissue-facing side 122 of the porous member 118) as shown in FIGS. 3 and 4. Other examples of patterns the tissue-fixation element 126 may take include, without limitation, islands or circles (uniform or random) as shown in FIG. 5, concentric circles as shown in FIG. 6, mesh as shown in FIG. 7, concentric squares, triangles, diamonds, or any other pattern. Typically, the pattern will involves less than 100 percent coverage of the second, tissue-facing side 127 of the fluid-permeable substrate member 124 (or alternatively the second, tissue-facing side 122 of the porous member 118), but if a tissue-fixation element 126 is used that allows fluid migration through the tissue-fixation element 126, 100 percent (100%) coverage may be used. As non-limiting examples, in FIG. 3, $A_t$ is approximately 25% (0.25) of $A_s$, and in FIG. 4, $A_t$ is approximately 50% (0.5) of $A_s$.

The tissue-fixation element 126 may be a water-soluble adhesive or a non-water-soluble adhesive. In one illustrative embodiment, the tissue-fixation element 126 is a water-soluble adhesive that dissolves at least after one hour of contact with liquid and yet remains at least 10 minutes in contact with a liquid. In another illustrative embodiment, the tissue-fixation element 126 is an adhesive activated by contact with an aqueous liquid. In another illustrative embodiment, the tissue-fixation element 126 is a water-soluble adhesive that remains for at least ten minutes when in contact with a liquid and substantially dissolves at least within one hour or within three hours of contact with a liquid. In some embodiments using a water-soluble adhesive, if a user desires to increase the rate of dissolution of the tissue-fixation element 126, a saline solution may be injected into the porous member 118.

With the non-water soluble version of the tissue-fixation element 126, the extent of the tissue-fixation element 126 on the porous member 118 or fluid-permeable substrate member 124 is adequate to allow flow of reduced pressure through the distribution manifold 116 for treatment from the start and at the same time adequate to tack to keep the distribution manifold 116 in place even when directly opposed by the gravitation field 131. In some embodiments, the tackiness of the tissue-fixation element 126 may be varied in strength at different locations on the porous member 118 or fluid-permeable substrate member 124.

In embodiments using a non-soluble tissue-fixation element 126, a non-soluble adhesive may be used. Non-limiting examples of non-soluble adhesives include colloids, hydrogels, silicone, lastomers, acrylics, polyurethanes, and polyvinyl acetates. In embodiments using a water-soluble tissue-fixation element 126, a water-soluble dispersible adhesive may be used to form the tissue-fixation element 126. Non-limiting examples of soluble or water sensitive dispersible adhesives that might be used include the following: Polyvinyl alcohol (PVOH), polyvinyl pyrrolidone (PVP), polyethylene oxide (PEO), polypropylene oxide (PPO), modified cellulose (such as carboxymethyl cellulose [CMC]) and cellulose ethers, hydroxyl and carboxy modified polymers, such as poly acrylics, poly acrylates, poly amides, polyesters, and polyurethanes and their salts (for example sodium, potassium, and ammonium), polyacrylamides, gums such as guar and xanthan, polyethylene glycols. Also, water solubility may be triggered through a change in pH or by substitution. For example, formation of a sodium salt from a carboxyl group to form a sodium carboxylate may be the trigger. These changes may be brought about using external sources, such as adding a high pH solution to the dressing (wound) where a carboxy functionality (acidic) is neutralized and made water soluble, or the additive is within the polymer matrix, becoming active and mobile on the absorption of moisture (from the wound or and external source, e.g. instillation). One commercially available water soluble substance that may be sufficient is a "Water Soluble Tape," which is used in wave soldering of circuit boards, and is available from 3M of St. Paul, Minn. The tissue-fixation element 126 may be formed with various medicaments, e.g., silver, included to provide additional therapy benefits. The tissue-fixation element 126 may also be formed from gels or colloids that provide additional conditioning of the tissue site 102 or that might help reduce irritation near the tissue site 102 being treated.

As shown in FIG. 2, a release liner 129 may be used to cover the second, tissue-facing side 130 of the tissue-fixation element 126. The release liner 129 covers the second, tissue-facing side 130 of the tissue-fixation element 126 for storage or before the tissue-fixation element 126 is applied. The release liner 129 has a first side 135 and a second, tissue-facing side 137. In a stored state, the first side 135 of the release liner 129 is removably coupled to the second, tissue-facing side 130 of the tissue-fixation element 126.

Referring again primarily to FIG. 1, the reduced-pressure system 100 further includes a sealing member 132 for disposing over the distribution manifold 116 and a portion of intact epidermis 110 to create a sealed space 133 containing the distribution manifold 116. The sealing member 132 may be any material that provides a fluid seal. A fluid seal is a seal adequate to maintain reduced pressure at a desired site given the particular reduced-pressure source or subsystem involved. The sealing member 132 may, for example, be an impermeable or semi-permeable, elastomeric material. Elastomeric materials have the properties of an elastomer. Elastomeric generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of sealing member materials include a silicone drape, a 3M Tegaderm® drape, or a polyurethane (PU) drape such as one available from Avery Dennison Corporation of Pasadena, Calif.

The sealing member 132 may have an attachment device 134 on a tissue-facing side 136. The attachment device 134 may be used to hold the sealing member 132 against the patient's epidermis 110 or another layer, such as a gasket or additional sealing member. The attachment device 134 may take numerous forms. For example, the attachment device 134 may be a medically acceptable, pressure-sensitive adhesive that extends about a periphery or all of the sealing member 134. As additional examples, the attachment device 134 may be a double-sided drape tape, paste, hydrocolloid, hydro gel or other sealing devices or elements.

The reduced-pressure system 100 further includes a reduced-pressure source 138 that may be fluidly coupled to the sealed space 133 and to the distribution manifold 116. The reduced-pressure source 138 may be coupled by a reduced-pressure delivery conduit 140 to a reduced-pressure interface 142. The reduced-pressure source 138 may be an external source as shown in FIG. 1 and may be fluidly coupled with the reduced-pressure delivery conduit 140. Alternatively, the reduced-pressure source 138 may be incorporated into the porous member 118 or disposed adjacent to the distribution manifold 116. The reduced-pressure source 138 may be any device for supplying a reduced pressure, such as a vacuum pump, wall suction, micropump, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa), and more typically still between −100 mm Hg (−13.3 kPa) and −150 mm Hg (−19.9 kPa).

In some embodiments of the reduced-pressure system 100, the reduced-pressure interface 142 provides fluid communication to the sealed space 133. In one illustrative embodiment, the reduced-pressure interface 142 is a T.R.A.C.® Pad or Sensa T.R.A.C.® Pad available from KCI of San Antonio, Tex.

Reduced pressure generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the distribution manifold 116, reduced-pressure delivery conduit 140, and proximate the tissue site 102. As the hydrostatic pressure around the tissue site 102 approaches the desired reduced pressure, the flow may subside, and the reduced pressure may be maintained. Unless otherwise indicated, values of pressure stated herein are gauge pressures. The reduced pressure delivered may be constant or varied (patterned or random) and may be delivered continuously or intermittently. Consistent with the use herein, an increase in reduced pressure or vacuum pressure typically refers to a relative reduction in absolute pressure.

A liquid receptor 144 may be fluidly coupled to (or included as an aspect of) the distribution manifold 116 for receiving fluids from the patient 104 under the influence of reduced pressure provided by the reduced-pressure source 138. The liquid receptor 144 may be a canister 146 as shown in FIG. 1 or may be an absorbent layer associated with the distribution manifold 116.

Referring primarily to FIGS. 1 and 2, in operation according to one illustrative embodiment, the distribution manifold 116 is sized for the tissue site 102 by selecting an appropriately sized distribution manifold 116 or cutting the distribution manifold 116 to size. If applicable, the distribution manifold 116 is prepared for application by removing the release liner 129. The second, tissue-facing side 130 of the tissue-fixation element 126 is disposed adjacent to the tissue site 102. The tissue-fixation element 126 adheres, at least temporarily, to the tissue site 102. The distribution manifold 116 thus remains substantially adjacent to the tissue site 102. In this way, the patient 104 may have the tissue site 102 parallel to the gravitational field 131 and nonetheless the distribution manifold 116 will remain at the desired location on the tissue site 102. The distribution manifold 116 may remain against the tissue site 102 even when all exterior support has been removed such that the distribution manifold 116 is suspended by only the tissue-fixation element 126 and perhaps to some extent by the tissue site 102 itself. In other words, the distribution manifold 116 may be retained adjacent to the tissue site 102 without any additional tools or supports other than the tissue-fixation element 126.

The sealing member 132 may then be disposed over the distribution manifold 116 and a portion of the intact epidermis 110 to create the sealed space 133. The distribution manifold 116 is disposed in the sealed space 133. If not already applied, the reduced-pressure interface 142 may be applied to the sealing member 132. The reduced-pressure delivery conduit 140 may be fluidly coupled between the reduced-pressure source 138 and the reduced-pressure interface 142. The reduced-pressure source 138 is activated and reduced pressure is thereby supplied to the sealed space 133 and fluids may flow from the tissue site 102 to the liquid receptor 144. The pattern of the tissue-fixation element 126 may allow a contracting force to be experienced in 360 degrees at the tissue site 102 during treatment. The contracting force is developed by contraction of the distribution manifold 116 or the sealing member 132 under the influence of reduced pressure.

In embodiments using a water-soluble tissue-fixation element 126, the tissue-fixation element 126 initially retains the distribution manifold 116 adjacent to the tissue site 102 and then with time the tissue-fixation element 126 dissolves. In one illustrative embodiment, the tissue-fixation element 126 remains at least ten (10) minutes in contact with a liquid and dissolves at least within one (1) hour, two (2) hours, or three (3) hours of contact with liquid. Because of the partial coverage of second, tissue-facing side 122 of the porous member 118 or fluid-permeable substrate member 124 by the tissue-fixation element 126, reduced pressure may immediately flow through the distribution manifold 116 to the tissue site 102 and may do so with more available flow paths as the tissue-fixation element 126 dissolves. In other embodiments, using a non-water-soluble tissue-fixation element 126, the pattern of the tissue-fixation element 126 remains and allows adequate flow between portions of the tissue-fixation element 126 or the tissue-fixation element 126 itself may allow fluid flow through the tissue-fixation element 126, i.e., the tissue-fixation element 126 may be fluid permeable.

Figure 8:
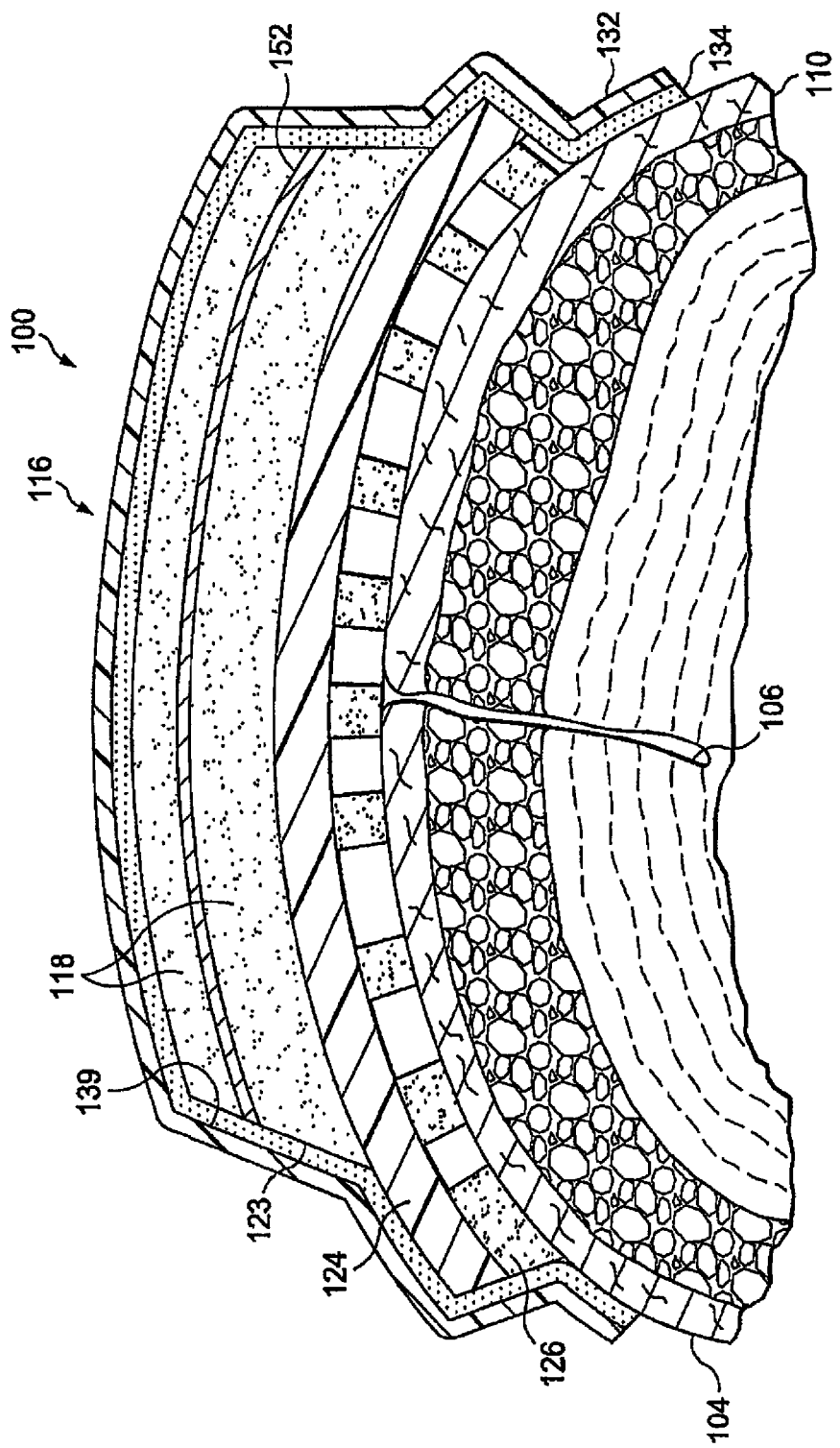
FIG. 8 is a schematic cross section of a portion of an illustrative embodiment of a reduced-pressure system for treating a tissue site.

Referring now primarily to FIG. 8, a portion of another illustrative embodiment of a reduced-pressure system 100 is presented. The reduced-pressure system 100 of FIG. 8 is analogous to the reduced-pressure system 100 of FIG. 1 with two main differences: a plurality of malleable members 152 have been added to the porous member 118 and the fluid-permeable substrate member 124 extends beyond the lateral edge 123 of the porous member 118.

The plurality of malleable members 152 plastically deform the distribution manifold 116 in order to accommodate a curved surface of the patient 104, such as a leg, arm, breast, or a complex surface. The plurality of malleable members 152 may be formed from steel or any plastically deformable members. While in cross section only one of the plurality of malleable members 152 is shown, it should be understood that any number of spaced members may be included. In operation, the distribution manifold 116 is plastically deformed to the shape of the curved surface of the patient 104 to be treated. The plurality of malleable member 152 retain the shape. The reduced-pressure system 100 may then be applied analogously to the deployment previously presented.

Figure 9:
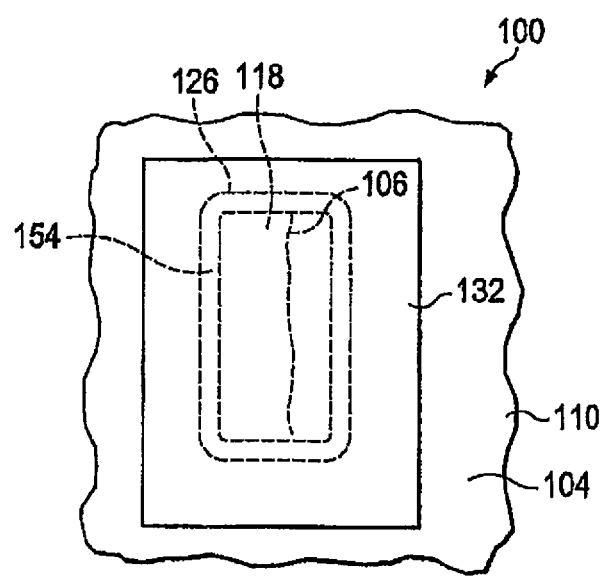
FIG. 9 is a schematic top view of a distribution manifold on a patient.

Referring now primarily to FIG. 9, a top view of a portion of another illustrative embodiment of a reduced-pressure system 100 is presented. The porous member 118 is shown with broken lines on an incision 106, which is also shown with broken lines. In this embodiment, the tissue-fixation element 126 extends beyond the porous member 118 to form an extension portion 154. The extension portion 154 helps off load forces to the epidermis 110 of the patient 104. In other embodiments, the fluid-permeable substrate member 124 may extend beyond the porous member 118 to offload forces.

Figure 10:
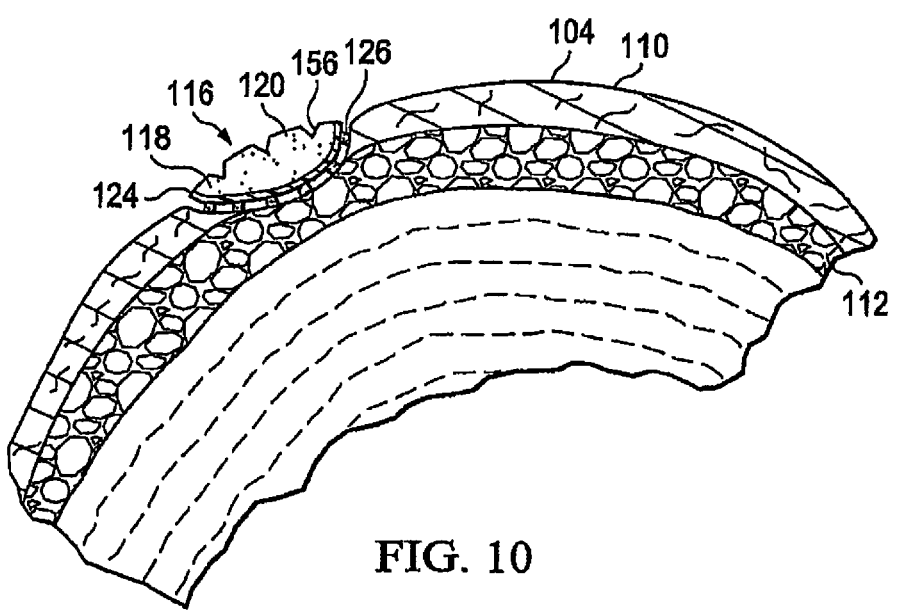
FIG. 10 is a schematic cross section of a portion of an illustrative embodiment of a reduced-pressure system for treating a tissue site.
Figure 11:
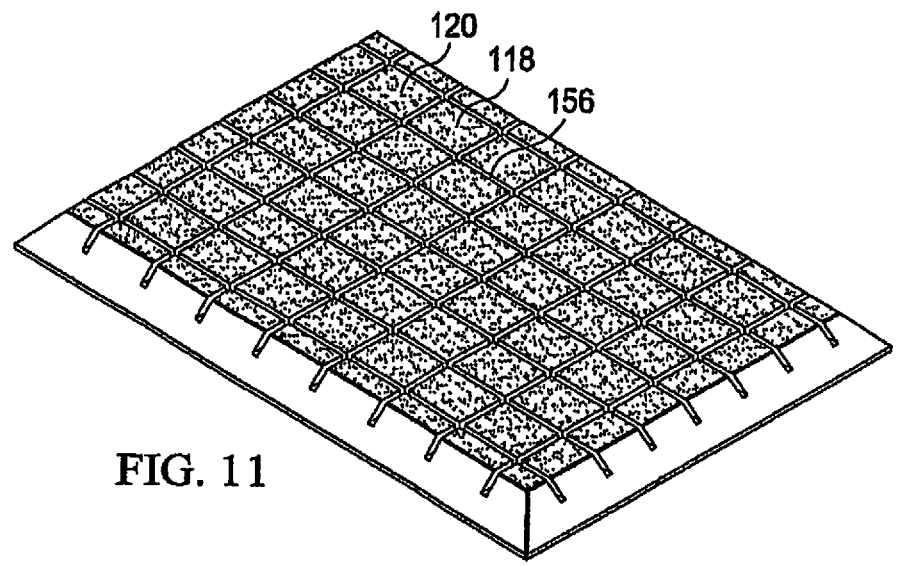
FIG. 11 is a schematic, perspective view of an illustrative embodiment of a porous member having notches.
Figure 12:
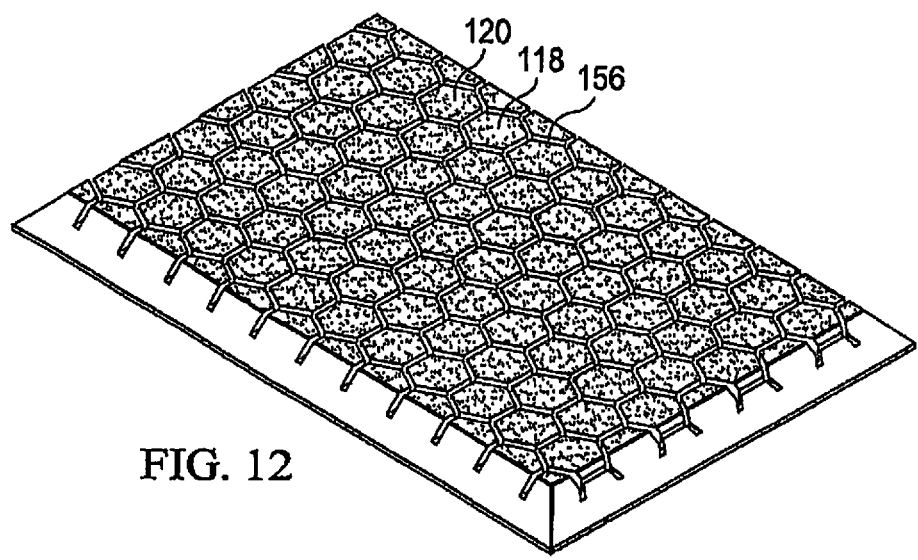
FIG. 12 is a schematic, perspective view of an illustrative embodiment of a porous member having notches.

Referring now primarily to FIG. 10, another illustrative embodiment of a distribution manifold 116 is presented. In FIG. 10, the sealing member 132 has not yet been applied. The distribution manifold 116 of FIG. 10 is analogous to the previous embodiments except that a plurality of notches 156 or cuts have been formed on the first side 120 of the porous member 118. The plurality of notches 156 help the distribution manifold 116 to flex or curve with a body part of the patient 104 or with movement of the patient's body. The plurality of notches 156 may be lateral cuts as suggested in FIG. 10, a grid or mesh pattern of cuts as shown in FIG. 11, hexagonal shaped cuts as shown in FIG. 12, or another shape.

In another illustrative embodiment, the tissue-fixation element 126 may be a liquid-activated adhesive. In such an embodiment, the tissue-fixation element 126 may be activated by liquids at the tissue site from the wound, saline, or skin preparation liquids. The user disposes the liquid-activated adhesive of the tissue-fixation element 126 against the tissue site 102 and allows the liquids present to activate the tackiness of the tissue-fixation element 126.

In another illustrative device, the tissue-fixation element 126 may be included as an aspect of the fluid-permeable substrate member 124. For example, in one illustrative embodiment, the fluid-permeable substrate member 124 may be a woven material with super absorbent fibers woven into the material. The super absorbent fibers become tacky when moistened. Other fibers or materials may be included in the fluid-permeable substrate member 124 to provide tackiness when moist, such as other water sensitive or crosslinked water soluble polymers (e.g., polyvinyl alcohol, carboxymethyl cellulose, alginates, and other natural gums such as xanthan and guar).

In another illustrative embodiment, a tissue-fixation element 126 may be stored separately with release liners, e.g., release liner 129, on both the first side 128 and the second, tissue-facing side 130. In use, the release liner is removed from the first side 128 and applied to the second, tissue-facing side 122 of the porous member 118 or the second, tissue-facing side 127 of the fluid-permeable substrate member 124. Then the release liner is removed from the second, tissue-facing side 130 of the tissue-fixation element 126, and the tissue-fixation element 126 is brought into contact with the tissue site 102. Alternatively, the release liner may first be removed from the second, tissue-facing side 130 of the tissue-fixation element 126 and applied to the tissue site 102. Then the release liner may be removed from the first side 128 of the tissue-fixation element 126 and the porous member 118 or fluid-permeable substrate member 124 applied adjacent to the tissue-fixation element 126. In another illustrative embodiment, the tackiness and strength of the tissue-fixation element 126 may be such that the tissue-fixation element 126 supplements the sutures or functions as sutures in holding an incision 106 in a closed position.

In another illustrative device, the sealing member 132 may be applied to the first side 120 of the porous member 118 and the tissue-fixation element 126 may be coupled to the second, tissue-facing side 127 of the fluid-permeable substrate member or the second, tissue facing side 122 of the porous member 118. The release liner 129 may cover the second, tissue-facing side 130 of the tissue-fixation element 126 and the second, tissue-facing side 139 of the sealing member 132. In this way, removing the release liner 129 in order to apply the sealing member 132 assures that the release liner 148 has also been removed from the tissue-fixation element 126.

With the illustrative embodiments herein, a distribution manifold 116 may be applied by a single user without requiring additional tools to hold the porous member 118 in place while the sealing member 132 is applied. Moreover, the user may have two hands available to apply the sealing member 132. The tackiness of the tissue-fixation element 126 may be such that the user may reposition the porous member 118 relative to the tissue site 102 before the sealing member 132 is applied.

In addition, the distribution manifold 116 may be applied with the patient in a prevailing position, which is a position that the patient will remain for a majority of time during treatment. This means a patient with a tissue site 102 that is on a vertical surface (parallel to the gravitational field 131) may have the distribution manifold 116 applied while remaining in the vertical position. In contrast, if a distribution manifold 116 on such a patient 104 is applied to the tissue site 102 in the horizontal position (orthogonal to gravitational field 131), when the patient again assumes a vertical position, they may find the distribution manifold 116 pulling and fitting in ways that are not comfortable to the patient.

Although the present invention and its advantages have been disclosed in the context of certain illustrative embodiments, it should be understood that various changes, substitutions, permutations, and alterations can be made without departing from the scope of the invention as defined by the appended claims. It will be appreciated that any feature that is described in connection to any one embodiment may also be applicable to any other embodiment. For example, the malleable members 152 of FIG. 8 may be included in the embodiment of FIG. 1.

We claim:

1. A reduced-pressure system for treating a tissue site, comprising:
   a porous member comprising a plurality of flow channels for distributing reduced pressure and receiving fluids, the porous member including a first side and a second side;
   a fluid-permeable substrate member comprising a fenestrated film and including a first side and a second side, wherein the second side of the porous member faces the first side of the fluid-permeable substrate member;
   a tissue-fixation element coupled to the second side of the fluid-permeable substrate member, wherein the tissue-fixation element has a tackiness strength that varies at different locations on the fluid-permeable substrate member; and
   a sealing member configured to be applied to the first side of the porous member and to create a sealed space.

2. The system of claim 1, wherein the porous member comprises foam.

3. The system of claim 1, wherein the fluid-permeable substrate member comprises a fenestrated drape.

4. The system of claim 1, wherein the fluid-permeable substrate member comprises polyethylene.

5. The system of claim 1, wherein the tissue-fixation element partially covers the second side of the fluid-permeable substrate member.

6. The system of claim 1, wherein the tissue-fixation element is configured to allow fluid flow between portions of the tissue-fixation element on the second side of the fluid-permeable substrate member.

7. The system of claim 1, wherein the tissue-fixation element comprises a spaced pattern configured to allow fluid flow between portions of the tissue-fixation element.

8. The system of claim 7, wherein the spaced pattern comprises a spaced pattern of circles.

9. The system of claim 1, wherein the tissue-fixation element comprises silicone.

10. The system of claim 1, wherein the tissue-fixation element is configured to be positioned adjacent to the tissue site.

11. The system of claim 1, wherein the tackiness strength of the tissue-fixation element relative to the tissue site is configured to be less than a bond strength between the tissue-fixation element and the fluid-permeable substrate member.

12. The system of claim 1, wherein the tissue-fixation element is configured to allow fluid to migrate through the tissue-fixation element.

13. The system of claim 1, wherein:
   the sealing member comprises an attachment device;
   the tissue-fixation element extends beyond the porous member to form an extension portion; and
   the attachment device is configured to hold the sealing member against at least the extension portion of the tissue-fixation element.

14. The system of claim 13, wherein the attachment device extends at least about a periphery of the sealing member.

15. The system of claim 13, wherein the attachment device is a pressure-sensitive adhesive.

16. The system of claim 1, wherein the porous member further comprises a plurality of cuts formed on the first side of the porous member and configured to provide flexibility.

17. The system of claim 1, wherein the second side of the porous member is coupled to the first side of the fluid-permeable substrate member.

18. The system of claim 1, wherein the second side of the porous member is directly coupled to the first side of the fluid-permeable substrate member.

19. The system of claim 1, wherein the fluid-permeable substrate member is configured to be positioned between the tissue site and the porous member.

20. The system of claim 1, wherein the fluid-permeable substrate member is disposed between the porous member and the tissue-fixation element.

21. The system of claim 1, further comprising a reduced-pressure source configured to provide reduced pressure to the sealed space.

22. The system of claim 21, further comprising a liquid receptor configured to receive fluids under the influence of reduced pressure from the reduced-pressure source.

23. A reduced-pressure system for treating a tissue site, comprising:
- a porous member comprising a plurality of flow channels for distributing reduced pressure and receiving fluids, the porous member including a first side and a second side;
- a fluid-permeable substrate member comprising a fenestrated film and including a first side and a second side, wherein the second side of the porous member faces the first side of the fluid-permeable substrate member, and wherein the fluid-permeable substrate member has a surface area $A_s$;
- a tissue-fixation element coupled to the second side of the fluid-permeable substrate member, wherein the tissue-fixation element comprises a spaced pattern, has a surface area $A_t$ where $0.15\, A_s < A_t < 0.4\, A_s$, and is configured to allow fluid flow between portions of the tissue-fixation element on the second side of the fluid-permeable substrate member; and
- a sealing member configured to be applied to the first side of the porous member and to create a sealed space.

24. The system of claim 23, wherein the spaced pattern comprises a spaced pattern of circles.

25. The system of claim 23, wherein the tissue-fixation element comprises silicone.

26. The system of claim 23, wherein the tissue-fixation element is configured to be positioned adjacent to the tissue site.

27. The system of claim 23, wherein a tackiness strength of the tissue-fixation element relative to the tissue site is configured to be less than a bond strength between the tissue-fixation element and the fluid-permeable substrate member.

28. The system of claim 23, wherein the sealing member comprises an attachment device on a tissue-facing side of the sealing member, wherein the tissue-fixation element extends beyond the porous member to form an extension portion, and wherein the attachment device is configured to hold the sealing member against at least the extension portion of the tissue-fixation element.

29. The system of claim 28, wherein the attachment device extends at least about a periphery of the sealing member.

30. The system of claim 28, wherein the attachment device is a pressure-sensitive adhesive.

31. A reduced-pressure system for treating a tissue site, comprising:
- a porous member comprising a plurality of flow channels for distributing reduced pressure and receiving fluids, the porous member including a first side and a second side;
- a fluid-permeable substrate member comprising a fenestrated film and including a first side and a second side, wherein the second side of the porous member faces the first side of the fluid-permeable substrate member;
- a tissue-fixation element coupled to the second side of the fluid-permeable substrate member and extending beyond the porous member to form an extension portion, wherein the tissue-fixation element comprises a spaced pattern of concentric circles and is configured to allow fluid flow between portions of the tissue-fixation element on the second side of the fluid-permeable substrate member; and
- a sealing member configured to be applied to the first side of the porous member and to create a sealed space, wherein the sealing member comprises an attachment device on a tissue-facing side of the sealing member, and wherein the attachment device is configured to hold the sealing member against at least the extension portion of the tissue-fixation element.

32. The system of claim 31, wherein the tissue-fixation element comprises silicone.

33. The system of claim 31, wherein the tissue-fixation element is configured to be positioned adjacent to the tissue site.

34. The system of claim 31, wherein a tackiness strength of the tissue-fixation element relative to the tissue site is configured to be less than a bond strength between the tissue-fixation element and the fluid-permeable substrate member.

35. The system of claim 31, wherein the attachment device extends at least about a periphery of the sealing member.

36. The system of claim 31, wherein the attachment device is a pressure-sensitive adhesive.

37. A reduced-pressure system for treating a tissue site, comprising:
- a porous member comprising a plurality of flow channels for distributing reduced pressure and receiving fluids, the porous member including a first side and a second side, and wherein the porous member further contains a plurality of cuts formed on the first side of the porous member and configured to provide flexibility, wherein the plurality of cuts form a grid pattern;
- a fluid-permeable substrate member comprising a fenestrated film and including a first side and a second side, wherein the second side of the porous member faces the first side of the fluid-permeable substrate member; and
- a tissue-fixation element coupled to the second side of the fluid-permeable substrate member, wherein the tissue-fixation element comprises a spaced pattern configured to allow fluid flow between portions of the tissue-fixation element.

38. The system of claim 37, wherein the spaced pattern comprises a spaced pattern of circles.

39. The system of claim 37, wherein the tissue-fixation element comprises silicone.

40. The system of claim 37, wherein the tissue-fixation element is configured to be positioned adjacent to the tissue site.

41. A dressing for treating a tissue site with reduced pressure, the dressing comprising:
  a porous member configured to distribute reduced pressure and receive fluids;
  a fenestrated film adjacent to the porous member;
  an adhesive adjacent to the fenestrated film and having a pattern that covers at least 20 percent and less than 40 percent of the fenestrated film; and
  a sealing member configured to be applied to the tissue site to create a sealed space.

42. The dressing of claim 41, wherein the adhesive is not water-soluble.

43. The dressing of claim 41, wherein the adhesive is silicone.

44. The dressing of claim 41, wherein the adhesive is silicone gel.

45. The dressing of claim 41, wherein the fenestrated film is polyethylene.

46. The dressing of claim 41, wherein:
  the adhesive is silicone gel; and
  the fenestrated film is polyethylene.

* * * * *